United States Patent [19]
Wright et al.

[11] Patent Number: 5,593,664
[45] Date of Patent: Jan. 14, 1997

[54] ANTIANGIOGENIC OLIGOMERS

[75] Inventors: Paul S. Wright, Cincinnati; Alan J. Bitonti, Maineville, both of Ohio

[73] Assignee: Merrell Pharmaceuticals Inc., Cincinnati, Ohio

[21] Appl. No.: 379,466

[22] PCT Filed: Jul. 20, 1993

[86] PCT No.: PCT/US93/06792
§ 371 Date: Apr. 5, 1995
§ 102(e) Date: Apr. 5, 1995

[87] PCT Pub. No.: WO94/04165
PCT Pub. Date: Mar. 3, 1994

Related U.S. Application Data

[63] Continuation of Ser. No. 55,950, Apr. 30, 1993, abandoned, which is a continuation of Ser. No. 932,111, Aug. 19, 1992, abandoned.

[51] Int. Cl.$^6$ .................. A61K 31/785; A61K 31/795
[52] U.S. Cl. ........................... 424/78.08; 514/930
[58] Field of Search .................... 514/824, 929, 514/930; 424/78.37, 78.08

[56] References Cited

U.S. PATENT DOCUMENTS

| | | |
|---|---|---|
| 3,528,949 | 9/1970 | Rutledge . |
| 4,027,038 | 5/1977 | Bernstein . |
| 4,071,524 | 1/1978 | Banitt . |
| 4,087,548 | 5/1978 | Lenhard . |
| 4,397,868 | 9/1983 | DeVries ................................. 504/48 |
| 4,724,235 | 2/1988 | Shanklin, Jr. . |
| 4,824,916 | 4/1989 | Kershner . |
| 4,868,210 | 9/1989 | Trivedi ................................. 514/539 |
| 5,019,556 | 5/1991 | Shapiro . |
| 5,039,529 | 8/1991 | Bergendal . |
| 5,424,063 | 6/1995 | Cardin et al. ........................ 424/78.08 |

FOREIGN PATENT DOCUMENTS

| | | |
|---|---|---|
| B3043974 | 1/1982 | European Pat. Off. . |
| 0043974 | 1/1982 | European Pat. Off. . |
| 0467185 | 1/1992 | European Pat. Off. . |
| 0781479 | 8/1957 | United Kingdom . |
| 2025406 | 1/1980 | United Kingdom . |
| 9200749 | 1/1992 | WIPO . |

OTHER PUBLICATIONS

D. S. Grant et al., Cell, vol. 58 pp. 933–943 (1989).
I. Vlodavsky et al., Israel Journal of Medical Sciences, vol. 24, pp. 464–470 (1988).
C. H. Blood et al., Biochimica et Biophysica Acta 1032, pp. 89–118 (1990).
J. Folkman, Perspectives in Biology and Medicine, 29:1, pp. 10–36 (1985).
N. Sakamoto et al., The Cancer Journal, vol. 2, No. 1, pp. 9–13, (1988).
J. Folkman et al., Science, vol. 221, pp. 719–725 (1983).
C. R. Parish, Int. J. Cancer, 40, pp. 511–518 (1987).
M. Nakajima et al., The J. of Biological Chemistry, vol. 259, No. 4, pp. 2283–2290 (1984).
G. H. Rong et al., Cancer, vol. 57, pp. 586–590 (1986).

*Primary Examiner*—Peter F. Kulkosky
*Attorney, Agent, or Firm*—Craig G. Svoboda

[57] ABSTRACT

The present invention relates to the use of certain anionic polyamide and polyurea oligomers for inhibiting angiogenesis, and for their use in treating diseases associated with angiogenesis. These oligomers have a number average molecular weight ($M_n$) less than 10,000, comprise recurring units coupled by carbonyl linking moieties and have predominantly linear geometry such that regular spacing between anionic groups exists in an aqueous medium. The oligomers also have a preferably linear backbone and be be in their salt form, preferably wherein the salt is pharmaceutically acceptable.

18 Claims, No Drawings

ANTIANGIOGENIC OLIGOMERS

The present application has an effective international filing date of Jul. 20, 1993 as application PCT/US93/06,792 which designated the U.S. and entered the U.S. national phase on Jan. 25, 1995 under 35 USC 371 and was assigned Ser. No. 08/379,466 and accorded a filing date of Apr. 5, 1995, which is a continuation of application Ser. No. 08/055,950 filed on Apr. 30, 1993, now abandoned, which is a continuation of application Ser. No. 07/932,111, filed on Aug. 19, 1992, now abandoned.

The invention relates to the use of certain anionic oligomers which inhibit angiogenesis. These compounds can be used in the treatment of, for example, atherosclerosis, tumors, and metastasis.

Angiogenesis or neovascularization is the process by which new blood vessels originate as capillaries. This process is necessary in certain beneficial processes, such as wound healing and embryogenesis. Angiogenesis is also believed to be an essential prerequisite to certain deleterious effects, such as tumor growth and diabetic retinopathy. Nonvascularized tumors remain small in size, typically less than a few millimeters in diameter. The size of such tumors, both primary solid tumors and metastatic tumors, is limited by the ability of nutrients to diffuse into the tumor. Once vascularized however, tumors can grow rapidly and quickly become a clinical problem. Evidence suggests that tumors release a substance, termed tumor angiogenesis factor, which stimulates nearby endothelial cells to produce capillaries. Thus, if the ability of the tumor cell to release tumor angiogenesis factor could be suppressed or if the substance, once released could be rendered ineffectual, primary and metastatic tumor implantation or growth once implanted could be prevented and disease suppressed.

Other deleterious conditions are known to be associated with neovasularization, such as neovascular diseases of the eye, such as retrolental fibroplasia, diabetic retinopathy, and neovascular glaucoma. Such conditions, as well as tumors and tumor metastasis, could be treated by administration of an anti-angiogenesis agent. Heparin and heparin sulfate have been reported to be effective for these purposes.

Applicants have discovered that a class of synthetic oligomers are heparinmimetic in that this class of oligomers inhibits proliferative activity by means of anti-angiogenic activity. Such oligomers would thus be useful in the treatment of a variety of diseases and conditions associated with angiogenesis.

SUMMARY OF THE INVENTION

This invention relates to the use of anionic polyamide and polyurea oligomers of formulae 1a and 1b, respectively,

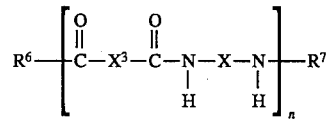

1a

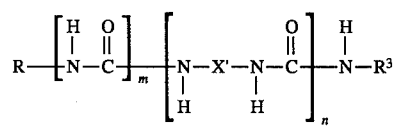

1b wherein $X$ and $X^3$ each independently represent either a phenylene group of the formulae

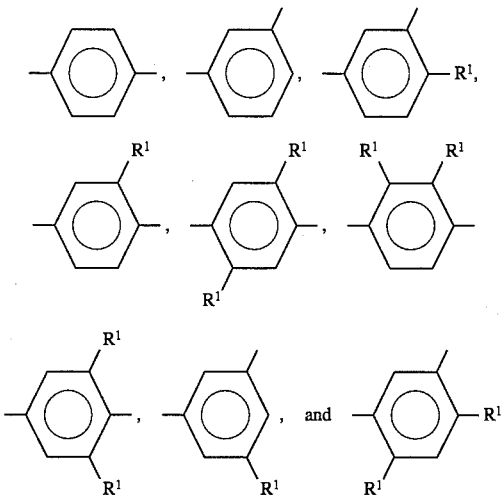

or a biphenylene group of the formula

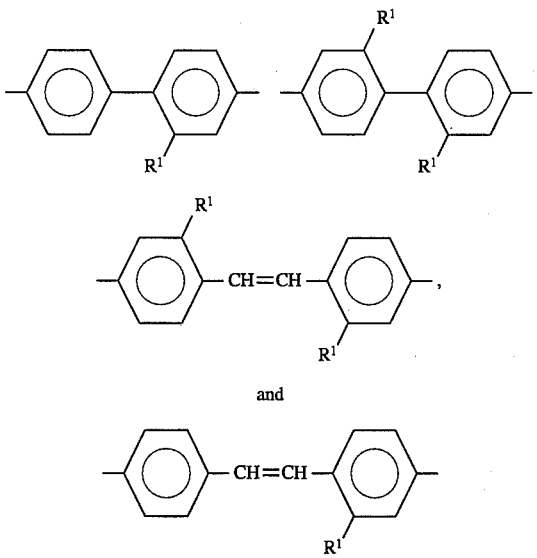

with the proviso that in a compound of formula 1a at least one of $X$ and $X^3$ must be a biphenylene moiety;

$X''$ is a group of the formulae

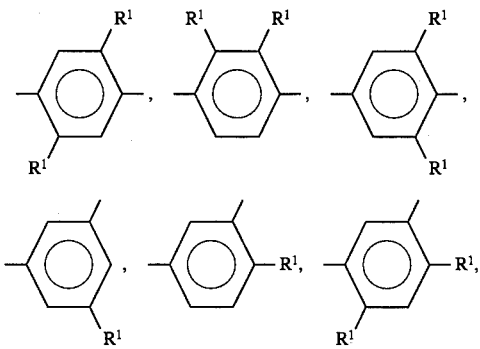

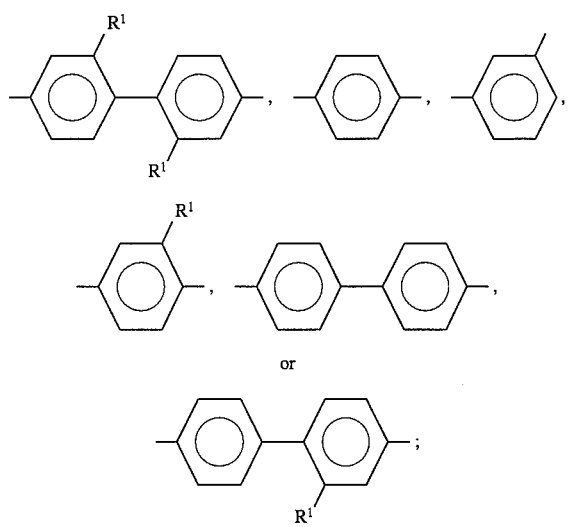

m is an integer 0 or 1, with the proviso that in a compound of formula 1b when m is 0, R is a hydrogen atom;

X' can be selected from any of the phenyl or biphenyl groups of X and $X^3$;

n is an integer of from 3 to 50;

R represents a hydrogen atom, a $C_1$-$C_4$ alkyl group, a phenyl group, or a phenyl group optionally substituted with 1 or 2 substituents selected from —$SO_3R^2$, —$CO_2R^2$, —$PO_3(R^2)_2$, or —$OPO_3R^2$ and optionally substituted with from 1 to 3 substituents selected from chloro, bromo, or $C_1$-$C_4$ alkyl;

$R^1$ represents —$SO_3R^2$, —$CO_2R^2$, —$PO_3(R^2)_2$, or —$OPO_3R^2$;

$R^2$ represents a hydrogen atom or a pharmaceutically acceptable cation;

$R^3$ represents —R or —X"—$NH_2$, where R and X" are defined as before;

$R^6$ represents $H_2N$—X"—NH—, $R^2O$—, RNH—, or R—C(=O)—NH—X"—NH—; and $R^7$ represents a hydrogen atom, $R^2O$—C(=O)—X"—C(=O)—, R—C(=O)—, or RNH—C(=O)—X"—C(=O)—.

DETAILED DESCRIPTION OF THE INVENTION

The oligomers of the present invention are polyamides and polyureas having a number average molecular weight Mn of <10,000 comprising recurring units coupled by carbonyl linking moieties, said oligomer having anionic groups and predominantly linear geometry such that regular spacing between anionic groups exists in an aqueous medium. The oligomers are preferably linear in their backbone and also may be in their salt form. Particularly preferred salts are those that are pharmaceutically acceptable.

The term "pharmaceutically acceptable cation" means a cation acceptable for pharmaceutical use. Those cations that are not substantially toxic at the dosage administered to achieve the desired effect and do not independently possess significant pharmacological activity are included within the term "pharmaceutically acceptable cation". Illustratively, these salts include those of alkali metals, such as sodium and potassium; alkaline earth metals, such as calcium and magnesium; ammonium; light metals of Group IIIA including aluminum; and organic primary, secondary and tertiary amines, such as trialkylamines, including triethylamine, procaine, dibenzylaine, N,N'-dibenzylethylenediamine, dihydroabietylamine, N-($C_1$-$C_4$)alkylpiperidine, and any other suitable amine. Sodium and potassium salts are preferred. The term "pharmaceutically acceptable" means suitable for administration to warm blooded animals, especially human beings, and includes being nontoxic, e.g., suitable for pharmaceutical use and is not poisonous to the warm blooded animal. The pharmaceutically acceptable cations of the oligomers of the present invention are prepared by conventional ion exchange processes or by treating the $R^1$ acid with an appropriate base.

The oligomers of the present invention are low molecular weight, rigid backbone, water soluble polymers. Additionally, the oligomers have ordered anion spacing. By "ordered anion spacing" or "regular spacing between anionic groups" is meant that the anionic groups ($R^1$) are present in the backbone of the polymer at intervals determined by the starting material reagent used and the occurrence of the anionic groups is controlled in a predictable manner.

The terms "predominantly linear geometry" in an aqueous medium refers to the solution configuration of the oligomer. A method well known in the art for characterization of the solution configuration of polymer molecules is based on the following formula, referred to as the Mark-Houwink equation ["Introduction to Physical Polymer Science", ed. L. H. Sperling, pub. John Wiley & Sons, Inc. (1985), pp. 81–83], $$[\eta]=KM^\alpha$$

wherein $\eta$ is intrinsic viscosity; M is weight average molecular weight; K is a constant related to chain bond dimension; and $\alpha$ is a constant determined by polymer configuration. The intrinsic viscosity ($\eta$) for a random coil polymer is $0.5<\alpha<0.9$; and for a linear polymer is $0.98 \leq \alpha<1.8$. This formula relates the solution viscosity "$\eta$" to the molecular weight "M". For this invention linear polymers are defined as having "$\alpha$" values greater than or equal to 0.9. For a rigid rod polymer the theoretical upper limit is 1.8. For a given molecular weight, a higher solution viscosity will be obtained from polymers with a linear configuration relative to those polymers which exist as a random coil. An additional consideration is that the "$\alpha$" value is a function of the solvent used. The "$\alpha$" for a given water soluble polymer may be different at different salt concentrations. For this invention, the salt concentration is set at the levels present in serum (approximately 80 g/L NaCl, 4 g/L KCl).

As used herein, the term "oligomer" encompasses all the possible values for n, e.g., 3 through 50. The oligomers are preferably linear with n equal to an integer from 3 to 50, preferably from 3 to 20, more preferably from 3 to 15. Of course, the n value is directly related to the molecular weight of the resulting oligomer. It is essential that these oligomers are of sufficiently low molecular weight in order to pass through the renal excretory membrane, but able to inhibit angiogenesis. The average molecular weight is governed by the stoichiometry of the reagents. The number average molecular weight (Mn) is <10,000, preferably from about 400 to about 10,000, and most preferably from about 1,000 to about 6,000.

For the purpose of the present invention, the oligomers described herein and physiologically acceptable salts thereof are considered equivalent. Physiologically acceptable salts refer to the salts of those bases which will form a salt with at least one acid group of the $R^1$ group and which will not cause significant adverse physiological effects when administered as described herein. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary and tertiary amines and the like.

As for all generic groups of chemical compounds having pharmacological and therapeutic activity, some compounds and subgroups of compounds are preferred. Of those compounds of formulae 1a and 1b, those compounds wherein n is an integer of from 3 to 18 are preferred, with the compounds wherein n is an integer of from 5 to 15 being more preferred, and those compounds wherein n is an integer of from 5 to 9 being most preferred. Also of the compounds of formulae 1a and 1b, those compounds wherein the $R^1$ groups are a $—SO_3R^2$, especially those wherein the $R^2$ group is a pharmaceutically acceptable cation, most especially those wherein the cation is a sodium cation, are preferred.

Also preferred are those polyamide compounds of formula 1a wherein $R^6$ is an $R—C(=O)—NH—X''—NH—$ group, especially wherein R is an optionally substituted phenyl group, most especially those wherein R is a phenyl group or a 4-methylphenyl group and wherein X'' is a group of one of the formula;

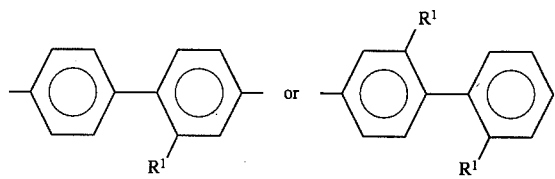

$X^3$ is a phenylene group, especially a paraphenylene group of the formula

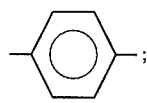

X is a biphenylene group, especially a biphenylene group of one of the formula

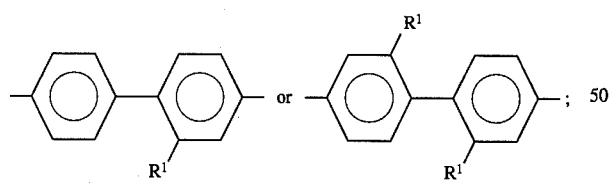

$R^7$ is an $R—C(=O)—$ group, especially wherein R is a phenyl group or a 4-methylphenyl group; and n is an integer of from 3 to 9, particularly the integers 5 or 9.

Also preferred are those polyurea compounds of formula 1b wherein

R is an optionally substituted phenyl group especially those wherein R is a phenyl group or a 4-methylphenyl group;

m is the integer 1;

X' is a phenyl or biphenyl group substituted by one or two $—SO_3R^2$ groups, especially those wherein $R^2$ is a sodium cation; and $R^3$ is an optionally substituted phenyl group especially those wherein R is a phenyl group or a 4-methylphenyl group.

Particularly preferred are those formula 1b compounds wherein

X' is a phenyl or biphenyl group of one of the following formulae

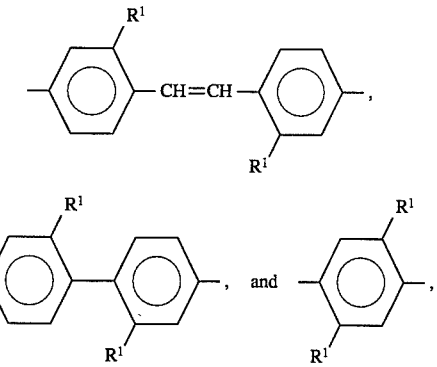

especially those wherein the $R^1$ group is a $—SO_3R^2$ wherein the $R^2$ group is a sodium cation.

The most preferred compounds are those of formula 1a wherein $R^6$ is a $RC(=O)NHX''NH—$ wherein R is a p-methylphenyl, X'' is a biphenyl group of the formula

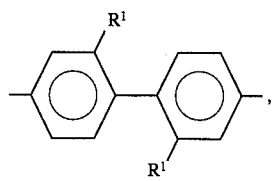

wherein $R^1$ is a $—SO_3R^2$, particularly where $R^2$ is a sodium cation;

$R^7$ is a $C(=O)R$ group where R is a p-methylphenyl;

$X^3$ is a paraphenylene group;

X is a group of the formula

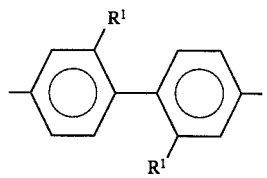

wherein $R^1$ is a $—SO_3R^2$ group, particularly where $R^2$ is a sodium cation; and n is the integer 5 or 9.

The oligomers can be prepared by the procedures described in European Patent Application 91111315.7, filed Jul. 8, 1991, published Jan. 22, 1992.

The ability of the sulfated oligomers of this invention to act as inhibitors of angiogenesis can be demonstrated by their ability to inhibit the tendency of human umbilical vein endothelial cells (HUVEC) cultured on basement membrane preparations to rapidly line up and form capillary-like structures in vitro. Differentiation of HUVEC, capillary tube formation, is not a proliferative response, as DNA synthesis drops off rapidly when the cells attach to the basement membrane components. These components include laminin, type IV collagen, enractin, and heparin sulfate proteoglycan.

Capillary formation in vitro has been used as an indicator to predict the capacity of compounds to promote or inhibit angiogenesis. Representative compounds of this invention were tested for their ability to block tube formation by HUVEC on commercially available basement membrane preparations (Matrigel). (See Example 2).

The amount of the sulfated oligomer of formula 1a or 1b to be administered can vary widely according to the particular dosage unit employed, the period of treatment, the age and sex of the patient treated, the nature and extent of the disorder treated, and the particular sulfated oligomer selected. Moreover the sulfated oligomer can be used in conjunction with other agents useful in inhibiting smooth muscle cell proliferation and angiogenesis and agents known to be useful to treat the symptoms of and complications associated with diseases and conditions caused by smooth muscle cell proliferation and angiogenesis. Antiangiogenesis and smooth muscle cell inhibitory effective amount of sulfated oligomer of formula 1 to be administered will generally range from about 15 mg/kg to 500 mg/kg. A unit dosage may contain from 25 to 500 mg of sulfated oligomer, and can be taken one or more times per day. The sulfated oligomer can be administered with a pharmaceutical carrier using conventional dosage unit forms either orally, parenterally, or topically.

The term "patient" used herein is taken to mean mammals such as primates, including humans, sheep, horses, cattle, pigs, dogs, cats, rats and mice.

The preferred route of administration is oral administration. For oral administration the sulfated oligomer can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The sulfated oligomers of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene-glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the sulfated oligomer of formula 1 in solution. Preservatives and buffers may also be used advantageously. In order to minimize or eliminate irritation at the site of injection, such compositions may contain a non-ionic surfactant having a hydrophile-tipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Definitions

The terms used in the present application are defined as follows:

n represents the number average repeat length of the distribution through all formulae.

MDL 101,028 and MDL 101,508 mean the compounds represented by Formula 1b above when R and $R^3$ are each a 4-methylphenyl; $R^2$ is sodium, X' is

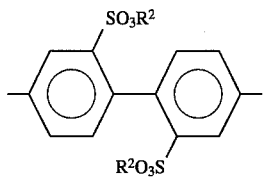

m is 1; and n is 6 and 9, respectively.

MDL 102,869 means a compound represented by formula 1b above wherein R and $R^3$ are each a 4-methylphenyl; m is 1; X' is

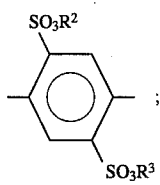

$R^2$ is sodium; and n is 15.

MDL 100,079 and MDL 100,023 mean the compounds represented by formula 1b above wherein R and $R^3$ are each a 4-methylphenyl; m is 1; X' is

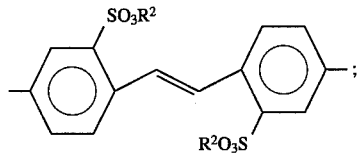

R2 is sodium; and n is 6 and 9, respectively.

MDL 100,758, MDL 101,995, MDL 100,127, and MDL 101,044 mean the compounds represented by formula 1a above wherein R is R—C(=O)—NH—X"—; R and $R^7$ are each a 4-methylphenyl;
$X^3$ is

X and X" are each

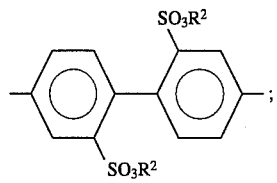

$R^2$ is sodium; and n is 3, 5, 6 and 9, respectively.

EXAMPLES

The following examples illustrate various aspects of the present invention:

Example 1

Effect of Anionic Polyamice and Polyurea Oligomers on Proliferation of Human Umbilical Vein Endothelial Cells (HUVEC)

Inhibition of Capillary Tube Formation In Vitro

Human umbilical vein endothelial (HUVEC) cultured on basement membrane preparations rapidly line up and form capillary-like structures in vitro. Differentiation of HUVEC, capillary tube formation, is not a proliferative response, as DNA synthesis drops off rapidly when the cells attach to the basement membrane components. These components include laminin, type IV collagen, enractin, and heparin sulfate proteoglycan. Capillary formation in vitro has been used as an indicator by others to predict the capacity of compounds to promote or inhibit angiogenesis. Previously, heparin fragments and the neparin analog, hexuronyl hexosaminoglycan sulfate, plus hydrocortisone have been shown to be negative regulators of angiogenesis. The Merrell Dow series of sulfated heparin-like polymers were tested for their ability to block tube formation of HUVEC on commercially available basement membrane preparations (Matrigel). The polymers were added when the HUVEC were seeded onto Matrigel, and left to coincubate. Tube formation was assessed visually with a microscope about 16 h after plating the cells. One of the most effective polymers tested, MDL 101044, completely prevented tube formation when added at 1 µM, and was somewhat inhibitory at 0.5 and 0.2 µM. Conversely, MDL 102869 was not effective at 2 µM and only partially inhibitory at 5 µM. The other polymers tested including MDL Nos. 101508, 101028, 100127, 100758, 100023, and 100079 completely inhibited tube formation at 2 and 5 µM. None of the polymers prevented endothelial cell attachment to Matrigel. Based on these findings it is likely that these polymers will be effective inhibitors of angiogenesis.

[$^3$H]Thymidine incorporation into DNA (trichloroacetic acid precipitable counts) was measured from HUVEC cultures seeded at $5 \times 10^4$ cells per well (12-well cluster plates, Costar). HUVEC and complete growth medium (EGM) were obtained from Clonetics (San Diego, Calif.). The compounds were incubated in the cultures for 24 hr, along with the [$^3$H]thymidine (1 µCi/ml), washed twice with phosphate buffered saline, then 0.25 ml 10% trichloroacetic was added and the cultures were chilled at 4° for 15 min. The acid was removed, and cellular material was solubilized with 0.25 ml 1N NaOH, neutralized with HCl, and CPM were measured by scintillanion counting. The numbers are means of duplicate cultures.

| COMPOUND*<br>(MDL NO.) | [3H]THYMIDINE<br>INCORPORATION | % CONTROL |
|---|---|---|
| Control | 32,308 | (100) |
| 101508 | 36,888 | 114 |
| 101028 | 49,565 | 153 |
| 101044 | 31,150 | 96 |
| 100127 | 40,496 | 125 |
| 100758 | 11,379 | 35 |
| 100023 | 53,468 | 165 |
| 100079 | 48,002 | 149 |
| 102869 | 41,507 | 128 |
| Heparin | 31,126 | 96 |

*Compounds were all added to cultures at 2 μM based on the polymers average molecular weight.

Example 2

Inhibition of Yolk Sac Neovascularization in Developing Chick Embryos with Anionic Polyamide and Polyurea Oligomers Compounds were dissolved in 0.5% methylcellulose, plus 60 μg hydrocortisone, then dried to a solid on teflon disks. The methylcellulose disk containing the test substances was placed on the yolk sac of developing chick embryos on day 4 after fertilization (using a shell-less culture method as described by Dunn et al., (1980) *Anat. Rec.* 199, 33–43). After 48 hours, neovascularization proximal to the methylcellulose disks was observed with a dissecting scope, and the response elicited by the compounds was scored independently by two investigators as inhibited (development of avascular zones or large decreases in microvessel densities) or uninhibited (no decreases or slight decreases in microvascular densities).

Previously, heparin fragments and the heparin analog, hexuronyl hexosaminoglycan sulfate, plus hydrocortisone have been shown to be negative regulators of angiogenesis in the yolk sac neovascularization assay.

| μg compound | MDL NUMBER | | | | |
|---|---|---|---|---|---|
| (per egg) | 100079 | 100127 | 101044 | 101995 | 101028 |
| 25 | 3/10# | ND** | 11/13 | 3/4 | 2/5 |
| 10 | 1/3 | ND | 5/6 | 5/7 | ND |
| 1 | 1/3 | 5/6+ | 2/3 | 4/5 | ND |
| 0.1 | 1/4 | ND | 1/6 | 2/4 | ND |
| 0.01 | 1/4 | ND | 1/3 | 1/3 | ND |

Control disks: 0.5% methylcellulose = 9/23; 60 μg hydrocortisone in 0.5% methylcellulose = 1/25; heparin (50 μg) plus hydrocortisone (60 μg) = 5/10.
The ratios represent the number of eggs showing inhibition of neovascularization/total number tested per condition.
**ND = not determined
+0.5 μg MDL 100127 plus 60 μg hydrocortisone per disk.

Example 3

Inhibition of Capillary Tube Formation by Human Umbilical Vein Endothelial Cells with Anionic Polyamide and Polyurea Oligomers Human endothelial cells were plated onto Matrigel at $5 \times 10^4$ (as described by Grant et al., 1989, Cell 58, 933–943) plus or minus the polymers as shown below. The ability of the compound to inhibit in vitro capillary tube formation was assessed 16 to 18 hr after plating.

| MDL No. | IC$_{50}$ μg/ml | IC$_{50}$ μM* | Inhibition at 10 μg/ml# |
|---|---|---|---|
| 101508 | ND** | MD | + |
| 101028 | 5 | 2 | + |
| 101044 | 5 | 1 | + |
| 100127 | 4–8 | 1–2 | + |
| 101995 | 6.4 | 2 | + |
| 100758 | ND | ND | + |
| 100023 | 4–8 | 1–2 | + |
| 100079 | 3–6 | 1–2 | + |
| 102869 | >25 | >5 | − |
| 101114 | >50 | >100 | − |
| Heparin | ND | ND | − |

*Concentration values are based on the average molecular weight of the polymers
+= complete inhibition of tube formation; −= no inhibition detected.
**ND = not determined Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method of inhibiting angiogenesis in a patient in need thereof which comprises administering to the patient an antiangiogenic amount of an anionic polyamide or polyurea oligomer of formulae 1a and 1b, respectively,

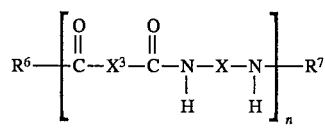

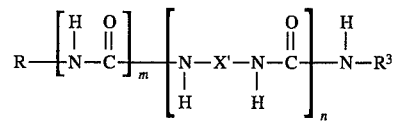

wherein

X and X³ each independently represent either a phenylene group of the formulae

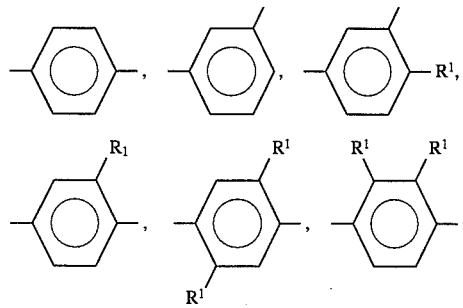

-continued

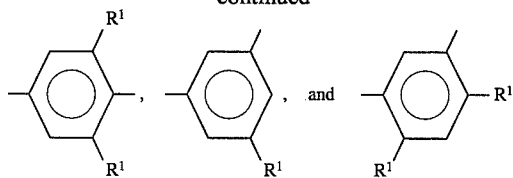

or a biphenylene group of the formula

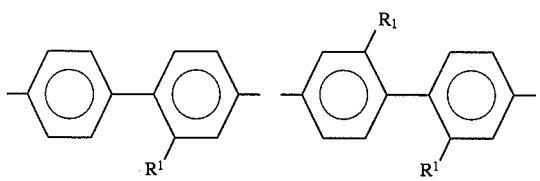

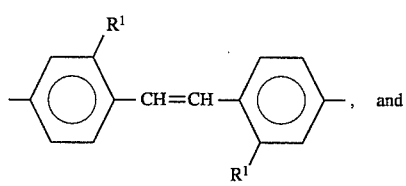

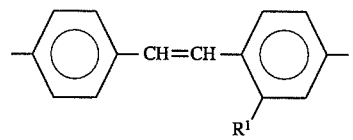

with the proviso that in a compound of formula 1a at least one of X and $X^3$ must be a biphenylene moiety;

X" is a group of the formulae

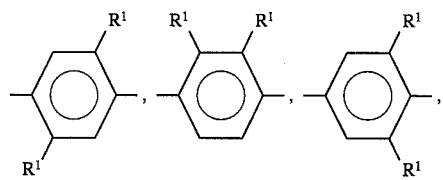

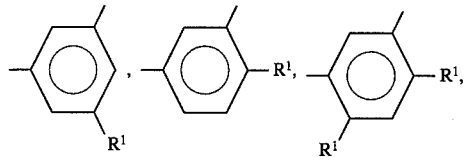

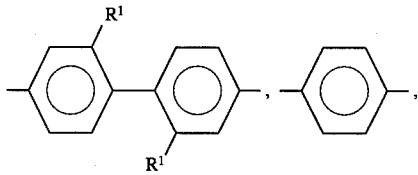

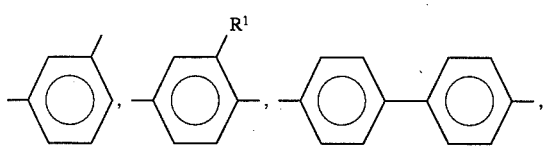

-continued

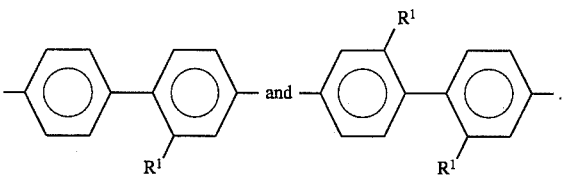

m is an integer 0 or 1, with the proviso that in a compound of formula 1b when m is 0, R is a hydrogen atom;

X' can be selected from any of the phenyl or biphenyl groups of X and $X^3$;

n is an integer of from 3 to 50;

R represents a hydrogen atom, a $C_1$-$C_4$ alkyl group, a phenyl group, or a phenyl group optionally substituted with 1 or 2 substituents selected from —$SO_3R^2$, —$CO_2R^2$, —$PO_3(R^2)_2$, or —$OPO_3R^2$ and optionally substituted with from 1 to 3 substituents selected from chloro, bromo, or $C_1$-$C_4$ alkyl;

$R^1$ represents —$SO_3R^2$, —$CO_2R^2$, —$PO_3(R^2)_2$, or —$OPO_3R^2$;

$R^2$ represents a hydrogen atom or a pharmaceutically acceptable cation;

$R^3$ represents —R or —X"—$NH_2$, where R and X" are defined as before;

$R^6$ represents $H_2N$—X"—NH—, $R^2O$—, RNH—, or R—C(=O)—NH—X"—NH—; and $R^7$ represents a hydrogen atom, $R^2O$—C(=O)—X"—C(=O)—, R—C(=O)—, or RNH—C(=O)—X"—C(=O)—.

2. A method of claim 1 wherein n is an integer of from 6 to 15.

3. A method of claim 1 wherein n is the integer 9.

4. A method of claim 2 wherein $R^1$ is a —$SO_3R^2$ group.

5. A method of claim 4 wherein $R^2$ is a sodium cation.

6. A method of claim 4 wherein $R^6$ is a R—C(=O)—NH—X"—NH— group.

7. A method of claim 6 wherein R is a phenyl or a 4-methylphenyl group.

8. A method of claim 6 wherein X" is a group of the formulae

9. A method of claim 4 wherein $R^7$ is a R—C(=O)— group.

10. A method of claim 9 wherein R is a phenyl or a 4-methylphenyl group.

11. A method of claim 4 wherein $X^3$ is a paraphenylene group.

12. A method of claim 4 wherein X is a group of the formula

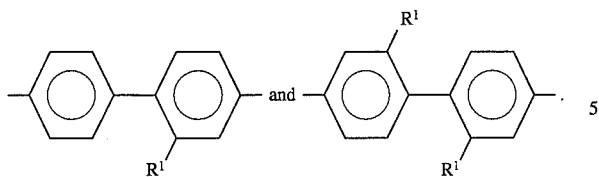 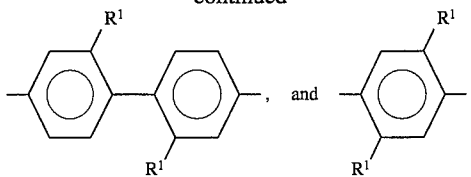

13. A method of claim 4 wherein $R^6$ is a R—C(=O)—NH—X''—NH—, $X^3$ is a paraphenylene group, X is a biphenylene group of the formulae,

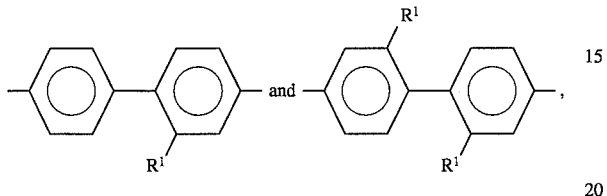

$R^7$ is a R—C(=O)— group, and R is a 4-methylphenyl group.

14. A method of claim 4 wherein m is the integer 1.

15. A method of claim 14 wherein R is a phenyl or 4-methylphenyl group.

16. A method of claim 14 wherein X' is a group of one of the formulae

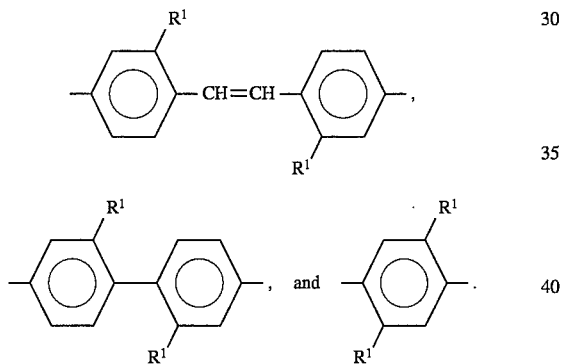

17. A method of claim 14 wherein R is a 4-methylphenyl group, X' is a group of the formulae

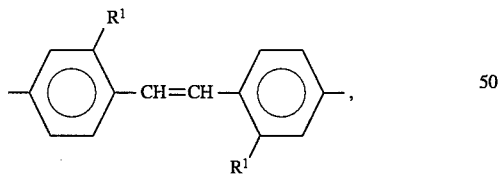

and $R^3$ is a 4-methylphenyl group.

18. A method of claim 1 wherein the oligomer is a polyurea of Formula I wherein R and $R^3$ are a 4-methylphenyl group; m is 1; n is 3 to 15; X represents

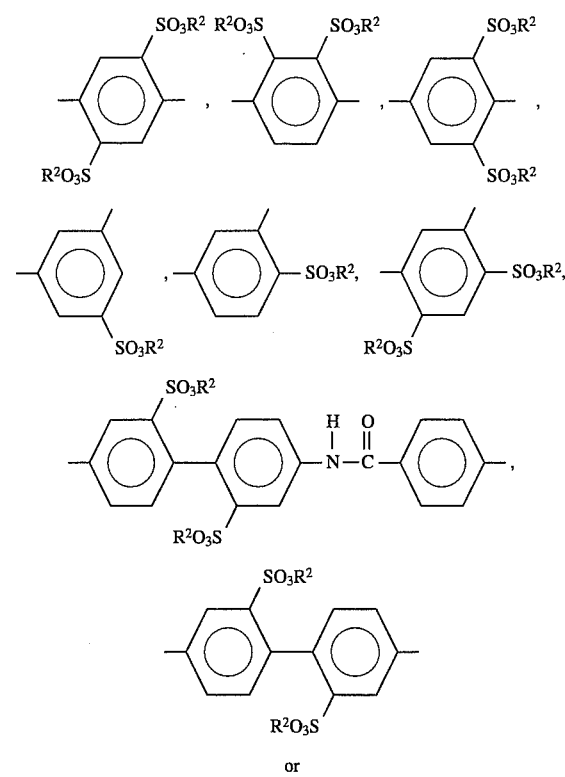

and $R^2$ is as defined as in claim 1.

* * * * *

UNITED STATES PATENT AND TRADEMARK OFFICE
CERTIFICATE OF CORRECTION

PATENT NO. : 5,593,664

DATED : January 14, 1997

INVENTOR(s) : Paul S. Wright, et al.

It is certified that error appears in the above-identified patent and that said Letters Patent is hereby corrected as shown below:

At column 8, line 30, the patent reads "tipophile" and should read --lipophile-- .

At column 10, line 21, the patent reads "polyamice" and should read --polyamide-- .

At column 12, line 32, the patent reads "polyamide or polyurea" and should read --polyamide and polyurea--.

Signed and Sealed this

Sixth Day of July, 1999

*Attest:*

Q. TODD DICKINSON

*Attesting Officer*      Acting Commissioner of Patents and Trademarks